US00PP24310P2

(12) United States Plant Patent
Heuger

(10) Patent No.: US PP24,310 P2
(45) Date of Patent: Mar. 11, 2014

(54) ***HELLEBORUS* PLANT NAMED 'COSEH 970'**

(50) Latin Name: ***Helleborus niger*×*Helleborus hybridus***
Varietal Denomination: COSEH 970

(76) Inventor: Josef Heuger, Glandorf (DE)

( * ) Notice: Subject to any disclaimer, the term of this patent is extended or adjusted under 35 U.S.C. 154(b) by 75 days.

(21) Appl. No.: 13/506,700

(22) Filed: May 10, 2012

(51) Int. Cl.
*A01H 5/00* (2006.01)

(52) U.S. Cl.
USPC ..... Plt./439; Plt./263.1

(58) Field of Classification Search
USPC ..... Plt./263.1, 439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 970', characterized by its upright and mounded plant habit; uniform and freely flowering habit; dark green-colored leaves; long flowering period; single greyed purple-colored flowers; and good garden performance.

2 Drawing Sheets

Botanical designation: *Helleborus niger*×*Helleborus hybridus*.

Cultivar denomination: 'COSEH 970'.

BACKGROUND OF THE INVENTION

The present invention relates to a new and distinct cultivar of *Helleborus* plant, botanically known as *Helleborus niger*× *Helleborus hybridus*, and hereinafter referred to by the name 'COSEH 970'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2005 of an unnamed proprietary seedling selection of *Helleborus niger*, not patented, as the female, or seed, parent with an unnamed proprietary seedling selection of *Helleborus hybridus*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2008.

Asexual reproduction of the new *Helleborus* plant by divisions in a controlled greenhouse environment in Glandorf, Germany since March, 2008 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 970'.

These characteristics in combination distinguish 'COSEH 970' as a new and distinct *Helleborus* plant:

1. Upright and mounded plant habit.
2. Uniform and freely flowering habit.
3. Dark green-colored leaves.
4. Long flowering period.
5. Single greyed purple-colored flowers.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus hybridus* 'COSEH 710', disclosed in U.S. Plant Pat. No. 21,063. In side-by-side comparisons conducted in Glandorf, Germany, plants of the new *Helleborus* differed from plants of 'COSEH 710' in leaf and flower color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 970' grown in a container.

The photograph on the second sheet is a close-up view of a typical flower of 'COSEH 970'.

DETAILED BOTANICAL DESCRIPTION

The aforementioned photographs and following observations, measurements and values describe plants grown during the winter in 17-cm containers in a glass-covered greenhouse in Glandorf, Germany and under environmental conditions and cultural practices which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus hybridus* 'COSEH 970'.

Parentage:

*Female, or seed, parent.*—Unnamed proprietary seedling selection of *Helleborus niger*, not patented.

*Male, or pollen, parent.*—Unnamed proprietary seedling selection of *Helleborus hybridus*, not patented.

Propagation:

*Type.*—By tissue culture.

*Time to initiate roots, winter.*—About two months at 12° C.

*Time to produce a rooted young plant, winter.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright and mounding plant habit with flowers held just above the foliar plane; plant shape is globose; moderately vigorous growth habit.

*Plant height.*—About 26.9 cm.

*Plant diameter* (*area of spread*).—About 50.3 cm.

Foliage description:

*Arrangement.*—Leaves arranged in a basal rosette; leaves palmately compound with about seven leaflets per leaf.

*Leaf length.*—About 14.5 cm.

*Leaf width.*—About 16.2 cm.

*Leaflet length.*—About 8.3 cm.

*Leaflet width.*—About 4.7 cm.

*Leaf shape.*—Palmate; orbicular in outline.

*Leaflet shape.*—Elliptic to obovate.

*Leaflet apex.*—Broadly acute.

*Leaflet base.*—Cuneate.

*Leaflet margin.*—Sharply serrate; slightly undulate.

*Leaflet texture, upper and lower surfaces.*—Smooth, glabrous; leathery.

*Leaflet venation pattern.*—Pinnate.

*Leaflet color.*—Developing leaves, upper surface: Between 144A and 146B; venation, close to N186C. Developing leaves, lower surface: Close to 146B; venation, close to 183B to 183C. Fully developed leaves, upper surface: Close to 147A; venation, close to 144B. Fully developed leaves, lower surface: Close to 146B; venation, close to 144C.

*Petiole.*—Length: About 11.5 cm. Diameter: About 5 mm. Texture, upper and lower surfaces: Smooth, glabrous. Color, upper and lower surfaces: Close to 144B; developing leaves heavily dotted with close to 183B.

Flower description:

*Flower shape and habit.*—Single rotate flowers arranged singly or in pairs; freely and uniform flowering habit with about 24 flowers and flower buds developing per plant; flowers facing outwardly to nodding.

*Fragrance.*—None detected.

*Natural flowering season.*—Plants begin flowering about ten months after planting; long flowering period, plants flower from late winter to early spring in Germany.

*Flower longevity on the plant.*—About ten days; flowers not persistent.

*Flower buds.*—Length: About 2.5 cm. Diameter: About 1.5 cm. Shape: Ovate. Color: Close to 185C to 185D.

*Flower diameter.*—About 5.8 cm.

*Flower depth* (*height*).—About 3 cm.

*Petals.*—Transformed into nectaries.

*Sepals.*—Quantity and arrangement: Five arranged in a single whorl. Length: About 3.5 cm. Width: About 2.9 cm. Shape: Broadly ovate to broadly elliptic. Apex: Rounded. Base: Cuneate. Margin: Entire, undulate. Texture, upper and lower surfaces: Smooth, glabrous. Color: When opening, upper surface: Between 185C and 186A; base, close to 146C. When opening, lower surface: Between 186A and N186D. Fully opened, upper surface: Close to 182B; base, close to 146C. With development, color becomes closer to 146B tinged with close to N199A. Fully opened, lower surface: Close to 183D; base, close to N186C.

*Peduncles.*—Strength: Moderately strong. Length: About 13.7 cm. Diameter: About 4 mm. Aspect: About 30° from vertical. Texture: Smooth, glabrous. Color: Close to 146C heavily dotted with close to 178A.

*Pedicels.*—Strength: Moderately strong. Length: About 3.2 cm. Diameter: About 2 mm. Aspect: Erect. Texture: Smooth, glabrous. Color: Close to 146C heavily dotted with close to 178A.

*Reproductive organs.*—Stamens: Quantity per flower: About 45. Filament length: About 1.5 cm. Filament color: Close to 155C. Anther shape: Reniform. Anther length: About 1.5 mm. Anther color: Close to 150D. Pollen amount: Scarce. Pollen color: Close to 4D. Pistils: Quantity per flower: About eight. Pistil length: About 1.1 cm. Stigma shape: Club-shaped. Stigma color: Close to 150D. Style length: About 1 cm. Style color: Close to 187A. Ovary color: Close to 145B; rib, close to 187B. Nectaries (transformed petals): Quantity per flower: About twelve. Length: About 7 mm. Diameter: About 2 mm. Shape: Narrow triangular, flattened tubular. Color: Close to 150A.

*Seeds and fruits.*—Seed and fruit development have not been observed on plants of the new *Helleborus*.

Garden performance: Plants of the new *Helleborus* have been observed to have good garden performance and to tolerate rain and wind; plants of the new *Helleborus* have been observed to tolerate high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 970' as illustrated and described.

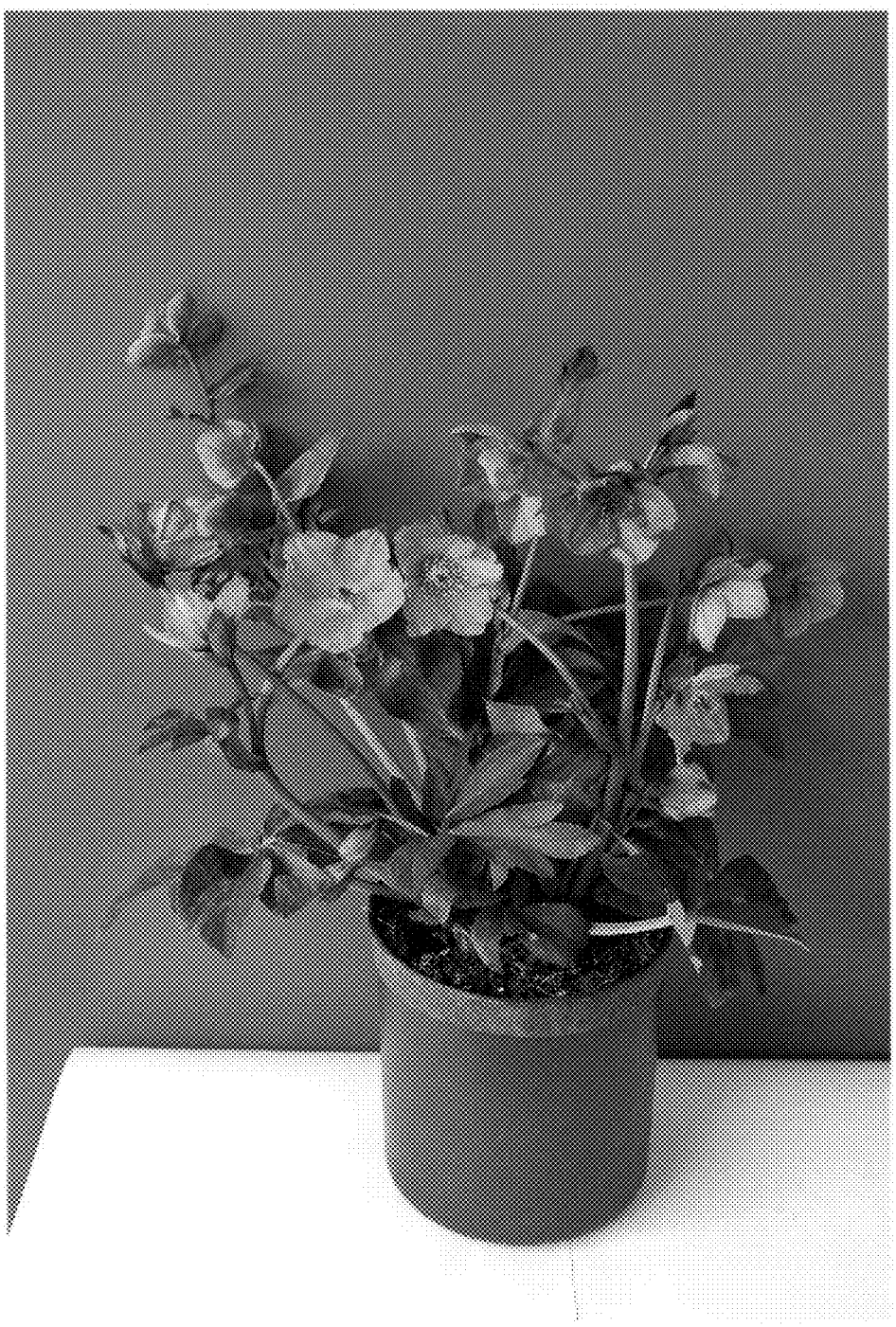

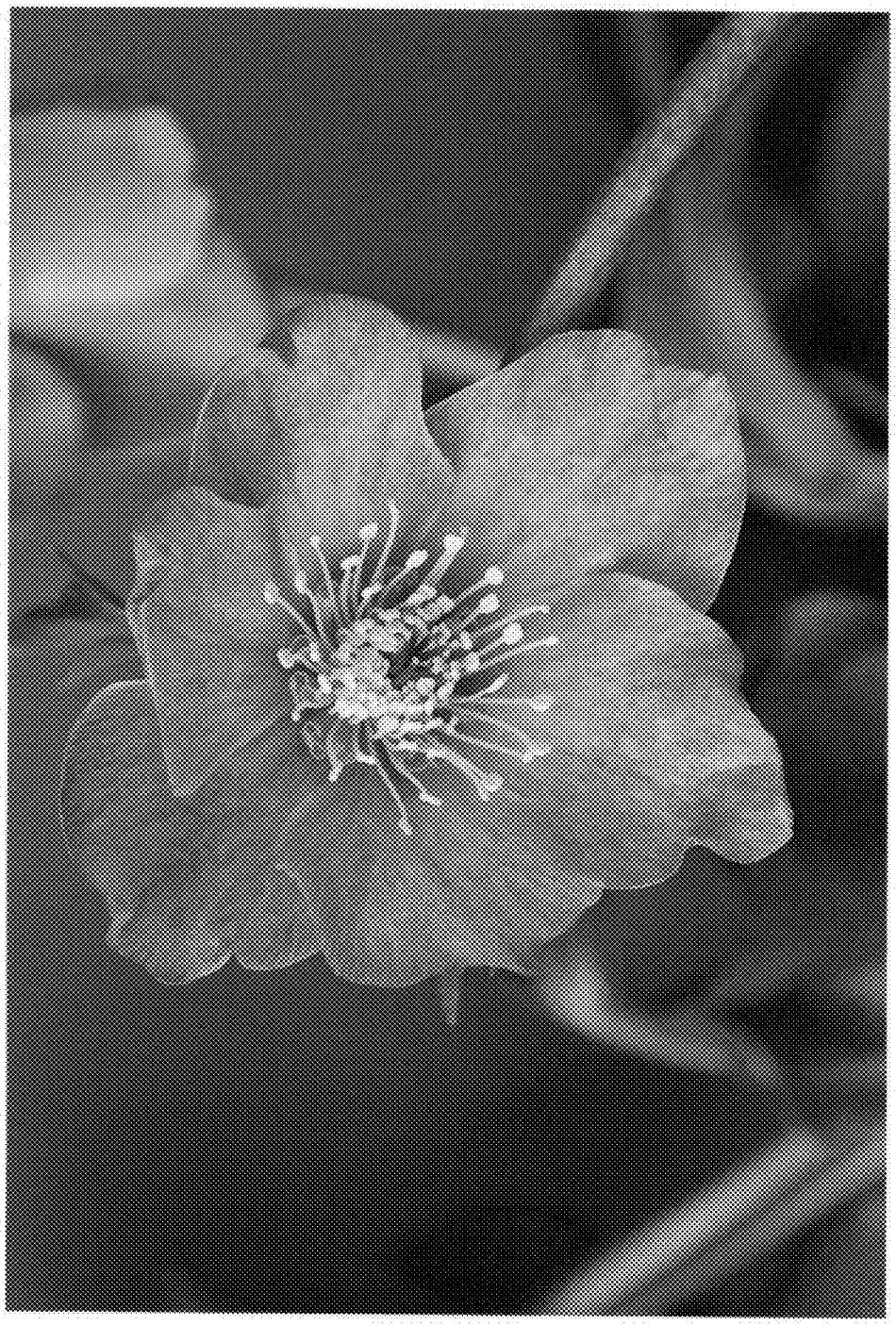

* * * * *